(12) United States Patent
Lau

(10) Patent No.: US 8,041,430 B2
(45) Date of Patent: Oct. 18, 2011

(54) TENS APPLICATION DEVICES

(76) Inventor: Kam Cham Lau, San Francisco, CA (US)

( * ) Notice: Subject to any disclaimer, the term of this patent is extended or adjusted under 35 U.S.C. 154(b) by 1219 days.

(21) Appl. No.: 11/787,240

(22) Filed: Apr. 16, 2007

(65) Prior Publication Data

US 2008/0255480 A1    Oct. 16, 2008

(51) Int. Cl.
    *A61N 1/18*      (2006.01)
(52) U.S. Cl. ............... 607/46; 607/48; 607/129
(58) Field of Classification Search .......... 607/46, 607/57, 67, 129, 142, 157, 48
See application file for complete search history.

(56) References Cited

U.S. PATENT DOCUMENTS

| | | | | |
|---|---|---|---|---|
| 4,112,941 A | * | 9/1978 | Larimore | 600/394 |
| 4,570,640 A | * | 2/1986 | Barsa | 600/554 |
| 5,400,782 A | * | 3/1995 | Beaubiah | 600/394 |
| 5,571,165 A | * | 11/1996 | Ferrari | 607/142 |
| 5,824,033 A | * | 10/1998 | Ferrari | 607/142 |
| 6,745,082 B2 | * | 6/2004 | Axelgaard | 607/142 |
| 6,907,299 B2 | * | 6/2005 | Han | 607/152 |
| 6,999,822 B2 | * | 2/2006 | Koike | 607/142 |
| 7,697,997 B2 | * | 4/2010 | Hyatt et al. | 607/142 |
| 2005/0015134 A1 | * | 1/2005 | Carim | 607/142 |
| 2005/0043655 A1 | * | 2/2005 | Schenck | 601/15 |

* cited by examiner

Primary Examiner — Brian T Gedeon
(74) Attorney, Agent, or Firm — David W. Wong

(57) ABSTRACT

A TENS currents application device has a composite laminated construction consisting of an electrical current conductive layer made of a carbon material sandwiched between a flexible outer layer and a body contact layer. The outer layer may be made of plastic or metal and has a plurality of magnet elements imbedded therein. A heating means may be additionally provided in the device. The device may be in the form of a disc or round ball which can be held in the palm of a patient or in the form of a sole insert which can be placed in the sole of a foot ware. Protruding points are additionally formed on the outer surface of the round ball and on the outer surface of the sole insert. A vibrating device is located in the handheld device for providing additional massaging function to enhance the TENS treatment.

3 Claims, 5 Drawing Sheets ions application device in the form a slipper or shoe insert

TENS APPLICATION DEVICES

BACKGROUND OF THE INVENTION

1. Field of the Invention

This invention relates to transcutaneous nerve stimulation and more specifically relates to devices for applying transcutaneous nerve stimulation for physiotherapeutic purposes.

2. Background Art

Transcutaneous nerve stimulation, commonly referred to as TENS is the application of a controlled amount of low electrical currents to stimulate nerves and/or muscle tissues in a patient for treating numerous physiological problems such as muscle and joint pain and inflammation. The currents may be provided in a steady flow or in electrical impulses of various wavelength frequencies. The electrical currents primarily stimulate the nerve for the body to produce natural endorphins to block the perception of pain and also physically cause the muscle tissues at the area of application to tighten and relax repeatedly, and thus increasing the blood circulation to enhance the natural curing process. The TENS currents are provided by a generator and the currents are delivered with application probes to the inflicted locations of a patient's body. The free end of the currents application probes is commonly in the form of a flexible inductive composite pad which must be attached to the patient's body with conductive adhesive gel and/or adhesive tapes in order to deliver the current to the patient's body. However, the curing process is not efficient if it is relying solely on the TENS stimulation.

Another problem in employing flexible TENS probes is that residual adhesive often remains on the patient's skin, which is difficult to clean off. Also, due to the natural skin secretion which hinders the affinity of the adhesive to the skin, the probes usually do not adhere securely in place particularly after repeated use. The adhesive probes are also particularly problematic to apply on skin area having body hair, as the probes would be difficult to remove from the patient without causing great discomfort and pain after the TENS treatment with the adhesive inherently pulling out hair from the skin area.

SUMMARY OF THE INVENTION

It is a principal object of the present invention to provide TENS application devices which are effective in providing efficient TENS treatment to a patient.

It is another object of the present invention to provide TENS application devices which include beneficial functions for providing enhanced TEN treatments to a patient.

It is another object of the present invention to provide TENS application devices having additional beneficial components for providing supplementary physiotherapy to a patient.

It is yet another object of the present invention to provide TENS application devices which may be located on selected areas of a patient's body without using adhesive.

It is still another object of the present invention to provide TENS application devices conveniently usable to deliver TENS treatment to a patient through the palms or sole.

BRIEF DESCRIPTION OF THE DRAWINGS

Other objects and advantages of the present invention will become apparent from the following detailed description of the preferred embodiments thereof in connection with the accompanying drawings wherein FIG. 1 a perspective front elevation view of the TENS application device according to the present invention for providing enhanced TENS treatment.

DETAILED DESCRIPTION OF THE PREFERRED EMBODIMENTS

Figure 1:
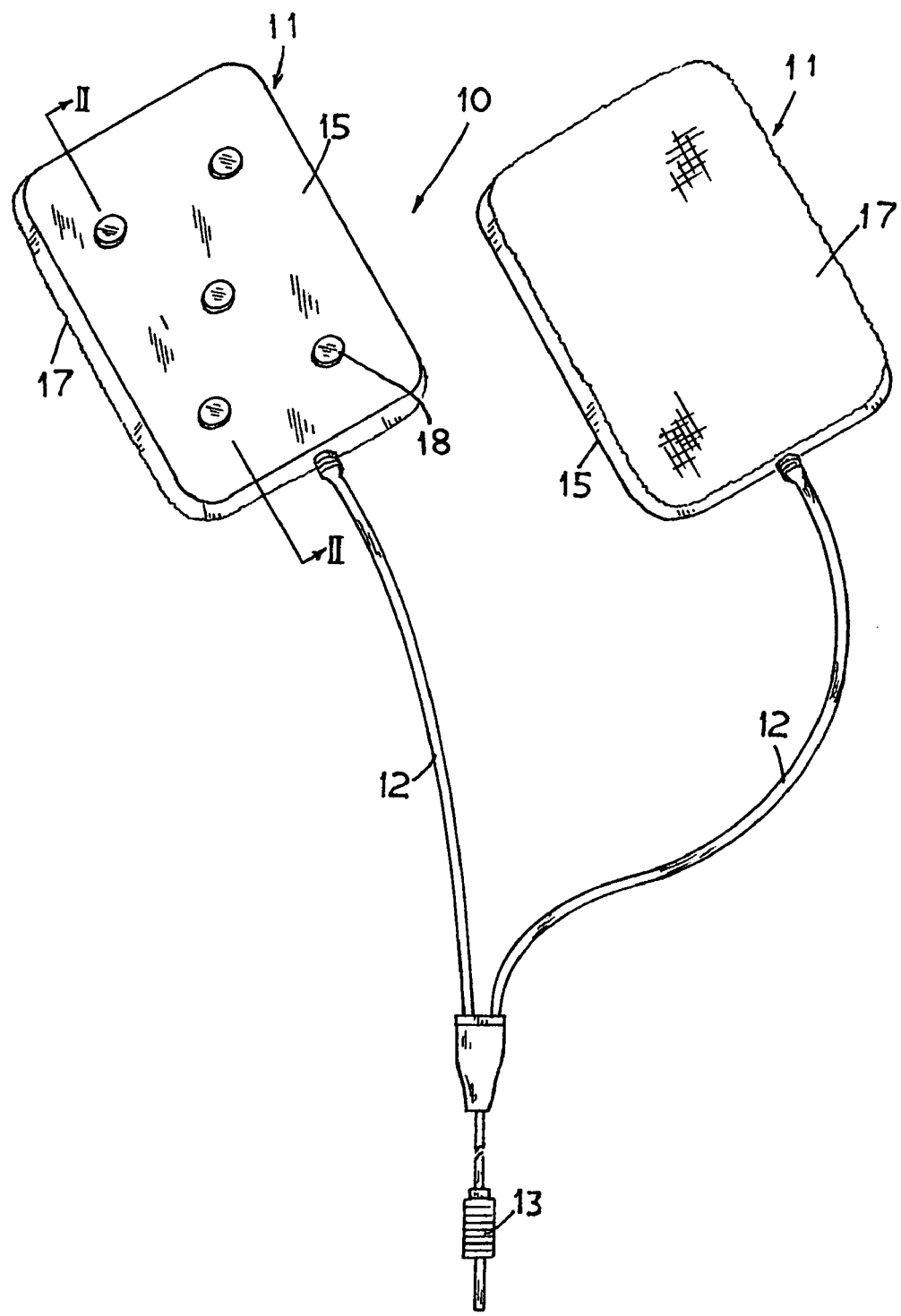
Figure 2:
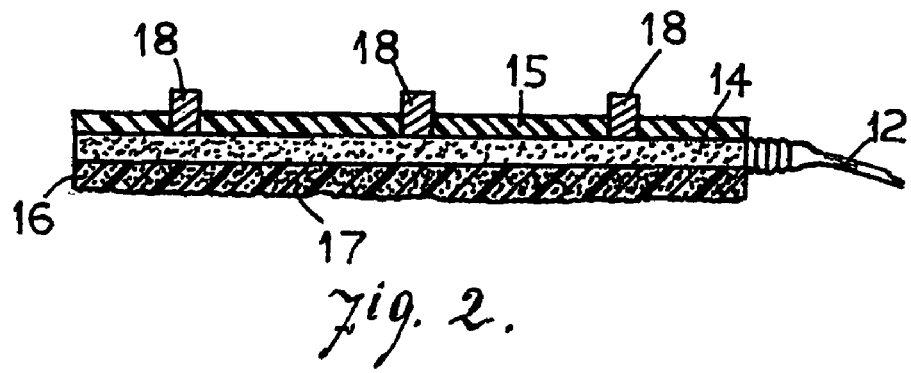
FIG. 2 is an enlarged isolated sectional side elevation view of the basic device according to the present invention along section line II-II in FIG. 1.

With reference to the drawings wherein like reference numerals designate corresponding parts in the several views, the TENS application device 10 of the present invention, applicable for providing enhanced TENS treatment for a patient as shown in FIGS. 1 and 2, has application probes 11 connected to a TENS generator (not shown) with a connecting cord 12 by an electrical connector 13. Each application probe 11 has a composite laminated structure including an electrically conductive carbon fiber center layer 14 sandwiched between an electrical insulated outer flexible layer 15 and an electrically conductive lower contact layer 16 for contacting with the patient's body. The electrical currents are conducted to the carbon fiber center layer 14 by the connecting cord 12. The probe 11 may be in any convenient shape such as rectangular, square, or round shape. A rectangular shape probe is shown as an exemplary embodiment for illustration purposes. The carbon fiber is preferably made of bamboo charcoal which has a porous structure and it possesses the characteristics of odor absorption, anti-bacteria, humidity adjustment, ultra infrared ray generation that can promote blood circulation, and negative ion generation, which can enhance the TENS treatment process. The upper layer 15 may be made of a flexible plastic or rubber compound and the like. The contact layer 16 may be made of a soft foam material having a coarse and liquid absorbent characteristics with a soft outer surface 17. A plurality of magnetic elements 18 are embedded in the outer flexible layer 15. The application probe 11 may be conveniently placed with its outer surface 17 of the body contact layer 16 in contact with the inflicted location on the body of a patient for the TENS treatment. Electrically conductive adhesive or gel may be provided on the outer surface 17 for attaching the probe 11 intimately to the patient. Alternatively, adhesive tapes may be employed for ensuring the attachment of the probe 11 to the body. The intensity of the currents can be varied by adjusting the TENS generator in the common manner. The magnetic elements 18 provide beneficial magnetic field to the treatment area to enhance the TENS treatment by increasing the blood flow to the inflicted area of the body.

Figure 3:
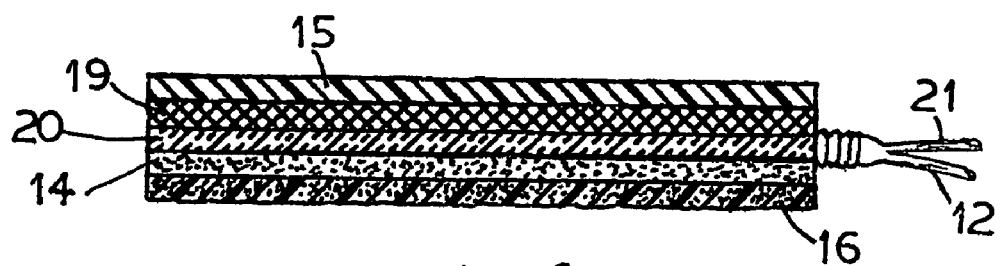
FIG. 3 is an enlarged isolated sectional side elevation view of another embodiment of the device of the present invention for providing enhanced TENS treatment.

FIG. 3 shows another embodiment of the application probe 11 of the present invention in which a heat generating layer 19 is provided in its laminated structure. The heat generating layer 19 may be located between the top layer 15 and the current conductive carbon layer 14 with or without an insulating spacer layer 20 provided between the carbon layer 14 and the heat generating layer 19. FIG. 3 shows the exemplary embodiment of having the insulating spacer layer 20 so that a warming heat is evenly transmitted the body contact layer 16. The heating layer 19 may be electrically actuated with a separate electrical connecting cord or alternatively the electrical supply cord may be combined with the connecting cord 12 as shown. During treatment the heat generating layer 19 is actuated to apply additional heat to the inflicted area of the patient to enhance the TENS. The heat will further enhance the blood circulation in the inflicted area for intensifying the natural physiotherapeutic process of the TENS currents. The positions of the TENS current conductive carbon layer 14 and the heat generating layer 19 may be alternatively located with the heat generating layer 19 located adjacent to the skin contact layer 16 so as to provide higher heat to the inflicted area of patient.

Figure 4:
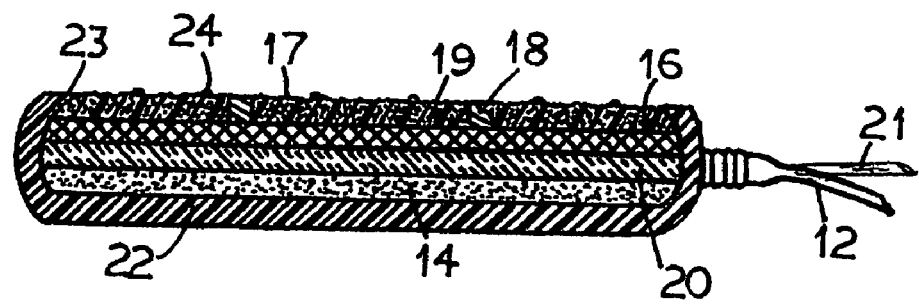
FIG. 4 is an enlarged isolated sectional side elevation view of another embodiment of the device of the present invention, which is applicable without the use of adhesive.

FIG. 4 shows another embodiment of the TENS probe of the present invention which is in the form of a rigid composite disk. The disk may have a round or other convenient shape for easy handling. This embodiment is a combination of that shown in both FIGS. 2 and 3. The device 10 in this embodiment is provided with a rigid outer plastic casing 22 having an opening 23. The laminated structure of the various layers is similar to that shown in FIG. 3. The exemplary illustration shows the construction with the heat generating layer 19 located adjacent to the body contact layer 16. A plurality of magnet elements 18 are also imbedded in the body contact layer 16. Additionally, a plurality of protruding points 24 extending outwards from the body contact layer 16 may also be provided on the outer surface 17. A composite electrical connecting cord 12 for supplying both the TENS current to the conductive carbon layer 14 and the heat generating layer 19 is shown. The device 10 in this embodiment, may be held by hand to press its body contact layer 16 tightly against the inflicted area of the patients body. The protruding points 24 provide a physical massaging excitation action in addition to the enhanced functions of the magnet elements 18 and heat generating layer 19 in the TENS treatment.

Figure 5:
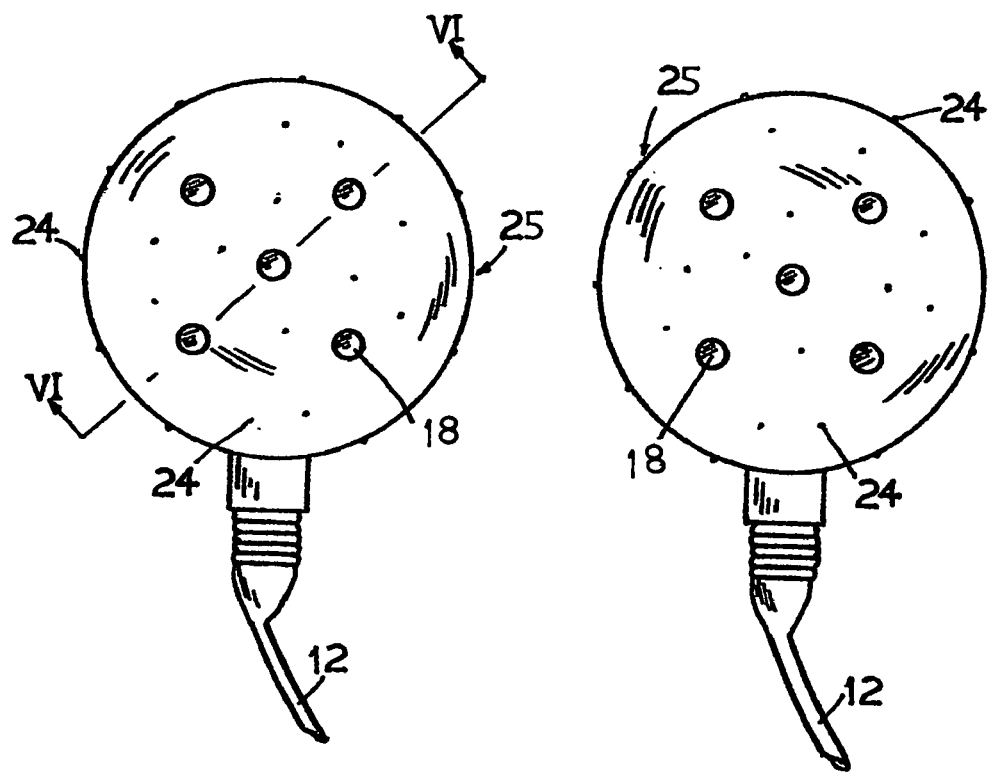
FIG. 5 is a perspective isolated front elevation view of the TENS application device in the form of a round ball operative for applying TENS through the palms of a patient.
Figure 6:
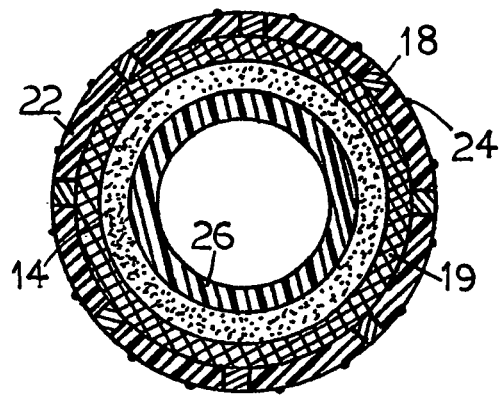
FIG. 6 is a sectional view of the round ball embodiment along section line VI-VI of FIG. 5.

FIG. 5 shows another embodiment in which the TENS application device 10 is provided with application probes 11 having a physical egg-shape or a round ball 25 so as to facilitate each application probe 11 to be held in the palm of the hands of a patient for applying the TENS treatment through meridian or pressure points in the palm rather than directly at various inflicted areas. As it is well known in eastern medicine, the palm possesses numerous meridian or pressure points having nerves which are directly linked with various internal organs and body parts of the human body as well as the central nerve system. Excitation of such meridian points will promote the functions of the related internal organs and body parts for providing their physiotherapeutic treatment. The handheld application device 25 may have a rigid outer layer 22 similar to the embodiment shown in FIG. 4 so as to enable it to be held tightly and intimately in the palm, which becomes the palm contact layer. A plurality of magnet elements 18 are imbedded in this outer layer 22 and a plurality of short protuberances or points 24 are formed on the external surface of the outer layer 22. These points 24 provide additional physical excitation of the meridian points of the palm when the probe 11 is gripped tightly for increasing the intensity of the TENS treatment. The probe 111 in this embodiment has a hard inner support layer 26 which may be a round shell as shown or alternatively a solid core. The concentric laminated structure of the embodiment includes a conductive carbon layer 14 and a heat generating layer 19 as in the above embodiments. The outer layer 22 may be also alternatively made of a hard plastic material or metallic material. Metallic material is preferred since it would provide increased intensity of TENS currents to the patient.

Figure 7:
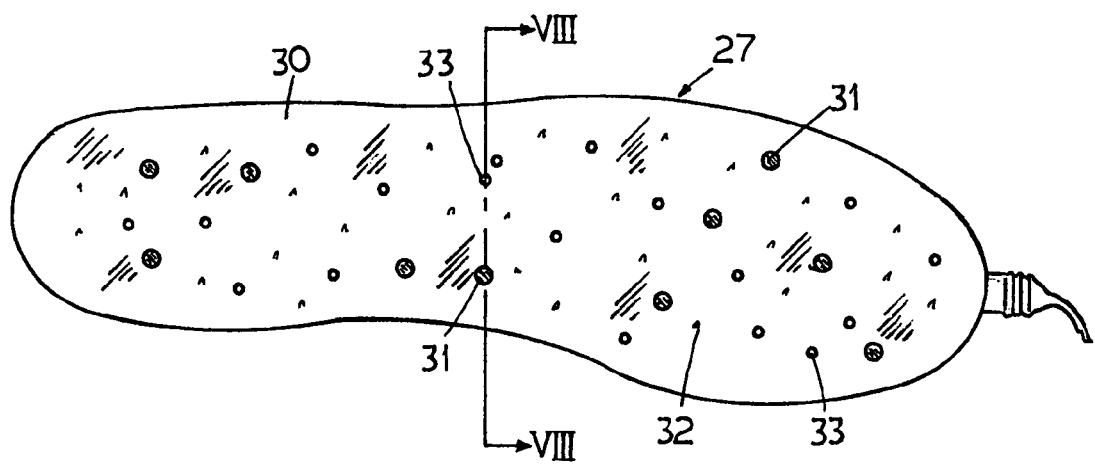
FIG. 7 is a perspective top elevation view of the TENS application device in the form a slipper or shoe insert according to the present invention operative for applying TENS through the patient's sole.
Figure 8:
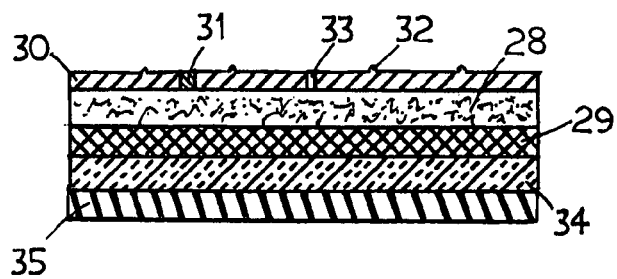
FIG. 8 is a sectional view along the sectional line VIII-VII of FIG. 7 showing the composite laminated structure of the device.

FIG. 7 shows another embodiment in which the probe 11 of the present invention is in the form of an insert pad 27 which may be provided in the insole of a foot ware such as slippers or shoes for applying the TENS currents to meridian or pressure points at the patient's sole. Similar to the palms, the meridian or pressure points at the sole also have nerves directly linked to internal organs and the central nerve system so that application of TENS currents at these points also can provide the desirable physiotherapeutic treatment. The power supply connecting cord 12 may be provided at the front end of the pad 27 and it may extend outward through the front of the slippers or the shoes which are to be worn by the patient either sitting or standing still during treatment. As shown in FIG. 8, similar to the above embodiments, the insert pad 27 has a composite laminated structure with a carbon fiber layer 28 sandwiched between a lower heating layer 29 and a top metal layer 30. A plurality of magnet elements 31 are imbedded in the top metal layer 30 and a plurality of upstanding protuberances or points or fingers 32 may also be formed on the upper surface therein. Additionally, a plurality of breath openings 33 are formed in the top metal layer 30, which enable the carbon fibers to absorb the humidity and odor from the foot of the patient. A protective insulation layer 34 is provided below the heating layer 29 which will be located juxtaposed to the sole 35 of the slipper or shoe. The insert pad 27 operates in the manner similar to the probe embodiment shown in FIG. 4.

Figure 9:
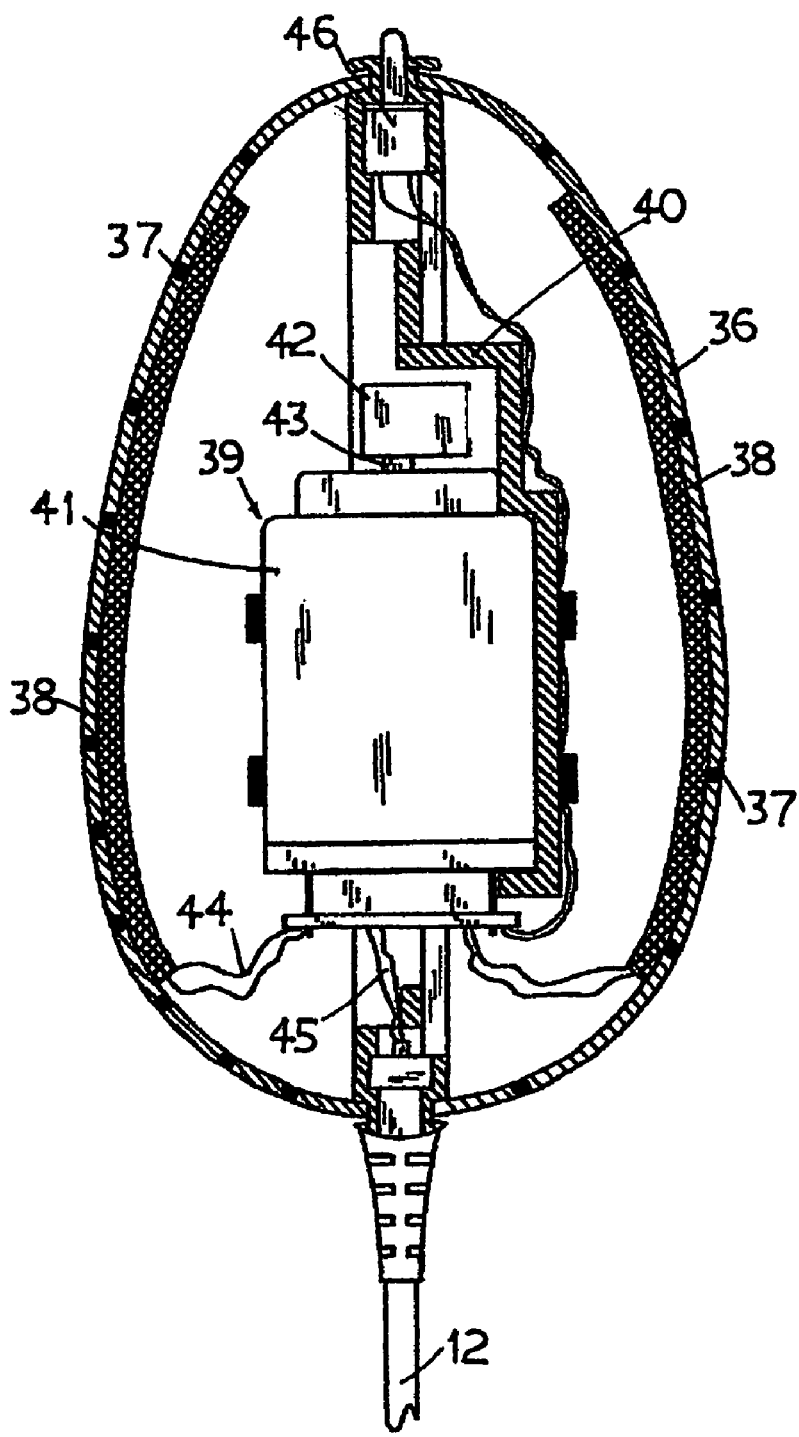
FIG. 9 is a partial sectional side elevation view of the TENS application device having a supplementary massaging component for providing enhanced TENS treatment without requiring adhesive for placing it on the patient.

Another handheld embodiment of the present invention is shown in FIG. 9. The device 10 in this embodiment has an outer shell 36 having an egg shape or round shape suitable for being held comfortably in the hand of the patient for the TENS treatment. An egg shape device is shown as an exemplary embodiment for illustration purposes. The outer shell 36 is made of metal having a plurality of magnet elements 37 imbedded therein. A heating layer 38 is provided on the inner side wall of the outer shell 36. A vibrating device 39 is mounted on a bracket 40 located inside the device. The vibrating device 39 comprises of a motor 41 having a rotary weight 42 mounted in an offset manner to the shaft 43 of the motor 41. Due to the offset mounting of the weight 42, its rotation will create a vibration movement of the device 10 for providing a massaging function. The heating layer 38 and the motor 41 are electrically connected to electrical supply and the TENS currents by lead wires 44 and 45 and connecting cord 12 respectively. The actuation of the vibrating device 39 is controlled by a switch 46 mounted on the outer shell 36 and located opposite to the connecting cord 12. The operation of this embodiment is similar to that shown in FIG. 5 with the additional vibration device 39 which may be selectively activated to provide the additional massaging function for enhancing the TENS treatment.

While the present invention has been shown and described in the preferred embodiments thereof, it will be apparent that various modifications can be made therein without departing from the spirit of the essential attributes thereof, and it is desired therefore that only such limitations be placed thereon as are imposed by the appended claims.

I claim:

1. A TENS application device for applying TENS treatment to a patient, comprising
   a multi-layer composite laminated member having an electrically insulative outer layer, an electrically conductive patient body contract layer and an electrical current conductive layer sandwiched between said outer layer and said patient body contact layer,
   a heating layer located between said outer layer and said current conductive layer,
   a connecting cord connecting said current conducting layer to a TENS currents generator and connecting said heating layer to a supply current,
   said current conductive layer being made of a carbon material,
   said outer layer being made of a flexible plastic material, and said patient body contact layer being a soft foam material having a liquid absorbent characteristic with a soft coarse external surface having a plurality of magnet particles imbedded therein.

2. A TENS application device according to claim 1 wherein said carbon material is a bamboo carbon fiber.

3. A TENS application device according to claim 2 further including a layer of insulating material located between said heating layer and said current conductive layer of carbon material.

* * * * *